United States Patent [19]

Miner

[11] Patent Number: 5,543,085
[45] Date of Patent: Aug. 6, 1996

[54] THICKENED NAIL POLISH REMOVER

[75] Inventor: Philip E. Miner, Newtown, Conn.

[73] Assignee: Chesebrough-Pond's USA Co., Division of Conopco, Inc., Greenwich, Conn.

[21] Appl. No.: 410,173

[22] Filed: Mar. 24, 1995

[51] Int. Cl.$^6$ .............................. A61K 7/047; C11D 1/62; C11D 3/37; C11D 3/43

[52] U.S. Cl. .................... 510/118; 424/61; 510/403; 510/404; 510/418; 510/493; 510/433; 510/434; 510/504

[58] Field of Search .................... 252/162, 170, 252/171, DIG. 8, 153, 174.24, 545, 547, 526, 528; 424/61

[56] References Cited

U.S. PATENT DOCUMENTS

| | | | |
|---|---|---|---|
| 4,032,464 | 6/1977 | Mausner | 252/89.1 |
| 4,197,212 | 4/1980 | Minton et al. | 252/164 |
| 4,412,027 | 10/1983 | Klein et al. | 524/364 |
| 4,781,916 | 11/1988 | Papaphilippou | 424/61 |
| 4,801,331 | 1/1989 | Murase | 106/5 |
| 4,804,486 | 2/1989 | Day | 252/153 |
| 4,986,936 | 1/1991 | Wolbert et al. | 252/170 |
| 5,024,779 | 6/1991 | Helioff et al. | 252/162 |
| 5,151,223 | 9/1992 | Maaser | 252/547 |
| 5,244,913 | 9/1993 | Coulter et al. | 514/358 |
| 5,338,345 | 8/1994 | Scarborough et al. | 106/2 |
| 5,342,536 | 8/1994 | Miner et al. | 252/162 |
| 5,346,652 | 9/1994 | Doloto et al. | 252/542 |
| 5,360,580 | 11/1994 | Doloto et al. | 252/542 |
| 5,373,025 | 12/1994 | Gay | 514/642 |

FOREIGN PATENT DOCUMENTS

| | | |
|---|---|---|
| 1154347 | 9/1983 | Canada . |
| 8704921 | 8/1987 | WIPO . |

OTHER PUBLICATIONS

Chemical Abstracts Registry File Listing for "Quaternium 14", registry No. 27479–28–3, 1995. no month available.

Primary Examiner—Paul Lieberman
Assistant Examiner—A. E. Hertzog
Attorney, Agent, or Firm—Milton L. Honig

[57] ABSTRACT

A polish-lacquer remover is provided that includes a volatile organic solvent, a thickening agent and an electrolyte. The most preferable combination is that of an acrylate/vinyl acetate cross polymer and 2-ethylhexyl alkyl ammonium methosulfate. Compositions of this invention are thickened but do not suffer from tacky or sticky residues upon solvent evaporation and have good lacquer removing efficacy.

3 Claims, No Drawings

THICKENED NAIL POLISH REMOVER

BACKGROUND OF THE INVENTION

1. Field of the Invention

The invention relates to a thickened nail polish remover that readily thins on application to nails and leaves no perceptible residue.

2. The Related Art

Products have long been marketed for the removal of nail polish (lacquer) from fingernails and toenails. These products essentially contain only a solvent with which to dissolve the lacquer. Typically the solvent will be a relatively volatile material such as acetone or ethyl acetate. Solvents render the product highly fluid.

Thicker formulations are desirable for several reasons. Better dose control can be achieved with higher viscosity products. Bottle spillage with a thicker material is less catastrophic than with a fluid which readily escapes its container. Improved targeting of lacquer also results from use of a less mobile remover.

A number of thickening systems exist for acetone based removers. Illustrative thickeners are alkyl vinyl ether copolymers as found in U.S. Pat. No. 5,024,779, hydroxypropyl cellulose as found in U.S. Pat. No. 4,197,212 and acrylic acid monomer and furanol as found in U.S. Pat. No. 4,804,486.

Traditional thickeners for polish removers such as Carbopol® (an acrylic acid polymer) and Klucel® (hydroxypropyl cellulose) do not readily thin on contact with the nail surface. Another problem is that they leave a gummy, sticky residue after the solvent evaporates.

Accordingly, it is an object of the present invention to provide a thickened nail polish remover that readily thins upon contact with the nails for ease and accuracy of dosing.

Another object of the present invention is to provide a thickened nail polish remover which upon application does not leave any perceptible residue after evaporation of solvent.

Still a further object of the present invention is to provide a thickened nail polish remover that upon solvent evaporation leaves no slimy or tacky film to cause pieces of an applicator cotton ball to stick against the nail or finger.

Still another object of the present invention is to provide a thickened nail polish remover that has improved lacquer removal efficacy.

These and other objects of the present invention will become more readily apparent through the following description of the invention.

SUMMARY OF THE INVENTION

A polish-lacquer removing composition is provided that includes:

(i) from about 50 to about 85% by weight of a volatile solvent having 2 to 10 carbon atoms and exhibiting a vapor pressure of more than 0.1 mm at 20° C.;

(ii) a thickening agent present in an effective amount to provide the composition with a viscosity ranging between 250 and 10,000 mPa—sec measured at 10 sec$^{-1}$ on a Haake CV 20 Rheometer; and (iii) an electrolyte present in an effective amount to raise conductivity of the composition to above 80 μmhos.

DETAILED DESCRIPTION OF THE INVENTION

Now a thickening system for volatile organic solvent polish removers has been found which no longer leaves a gummy or sticky residue after solvent evaporation. The composition can be applied with a cotton ball without fear that strands of the cotton will stick to a user's fingers. With the absence of any sticky residue, it is no longer necessary to wash fingernails before reapplication of fresh polish. The present invention achieves these results with a system that combines a thickening agent with an electrolyte.

Accordingly, a first essential element of compositions according to the present invention is that of a volatile organic solvent having from 2 to 10 carbon atoms with a vapor pressure of more than 0.1 mm, preferably of more than 0.5 mm at 20° C. Acetone and ethyl acetate are the volatile solvents of choice. These may, however, be utilized in combination with other solvents such as methyl ethyl ketone. Amount of the solvent will range from about 50 to about 85% by weight of the total composition. Preferably, the amount will range from about 60 to about 80%, optimally from about 70 to about 75% by weight.

A second essential element of compositions according to the present invention is that of a thickening agent. These agents may be selected from cellulose derivatives, natural gums, inorganic materials and synthetic homo- or co- polymers having from 1 to 30 carbon atoms per monomer unit. Examples of cellulose derivatives include sodium carboxymethyl cellulose and nonionic hydroxy- and hydroxyalkyl- cellulose (e.g. hydroxypropyl methyl cellulose, hydroxyethyl cellulose and hydroxypropyl cellulose). Examples of natural gums include acacia, alginate, carrageenan, guar, karaya, pectin, tragacanth and xanthan gums. Examples of inorganic materials are clays and silicas (e.g. fumed silica). Examples of synthetic polymers are those with monomers selected from the group consisting of acrylic acid and $C_1$–$C_{20}$ esters thereof, methacrylic acid and $C_1$–$C_{20}$ esters thereof, vinyl pyrrolidone, vinyl acetate, $C_2$–$C_{10}$ unsaturated carboxylic acids (e.g. maleic anhydride or acid), $C_2$–$C_{20}$ alkene and combinations thereof.

Particularly preferred among the thickening agents are crosslinked carboxylic copolymers formed from a mixture of monomers comprising (a) about 70 to 99% of a monoolefinically unsaturated carboxylic acid; and (b) about 0.1 to 5% of a crosslinking monomer selected from the group consisting of triallylisocyanurate, triallyl trimellitate and glyoxal bis(diallyl acetal). The carboxylic copolymers used in the invention may further comprise (c) about 1 to 15% of an additional comonomer containing a polymerizable ethylenically unsaturated group; and/or (d) about 0.1 to 3% of an ethoxylated glyceride compound of the formula

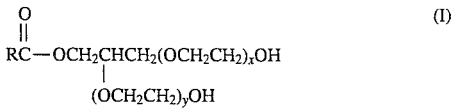

wherein R represents an alkyl group of from $C_8$ to $C_{18}$ and the sum of x+y is from 20 to 300. Most preferred is a copolymer of the aforementioned description with a CTFA name of acrylates/VA cross polymer, available from Rheox International, Inc., Hightstown, N.J. under the trademark Rheolate 5000.

Amounts of the thickening agent may range from about 0.001 to about 10%, preferably from about 0.01 to about 3%, optimally from about 0.1 to about 2% by weight of the composition.

A third essential element of compositions according to the present invention is that of an electrolyte. Suitable materials are inorganic salts and $C_4$–$C_{60}$ quaternary ammonium compounds. Illustrative salts include alkalimetal salts (e.g. lithium chloride, potassium bromide, sodium phosphate), alkaline earth metal salts (e.g. calcium bromide, magnesium chloride, calcium sulphate), aluminum salts (e.g. aluminum sulphate) and ammonium salts (e.g. ammonium chloride, ammonium sulphate, ammonium bromide).

Examples of the quaternary ammonium compounds useful for the present invention are illustrated by the general formula:

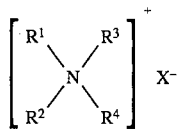

wherein $R^1$–$R^4$ can independently be selected from an aliphatic group having from 1 to 22 carbon atoms, $C_1$–$C_3$ alkyl, hydroxyalkyl, polyalkoxy or an aromatic, aryl or alkylaryl group having from 12 to 22 carbon atoms; and $X^-$ is an anion selected from halogen, acetate, phosphate, nitrate and $C_1$–$C_{16}$ alkylsulphate radicals. The aliphatic groups may contain in addition to carbon and hydrogen atoms, ether linkages, and other groups such as amino groups.

Other quaternary ammonium salts useful for the present invention have the formula:

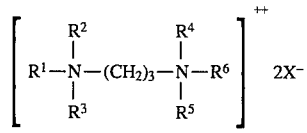

wherein $R^1$ is an aliphatic group having from about 16 to about 22 carbon atoms, $R^2$, $R^3$, $R^4$, $R^5$, and $R^6$ are selected from hydrogen and alkyl having from about 1 to about 4 carbon atoms, and $X^-$ is an ion selected from halogen, acetate, phosphate, nitrate and $C_1$–$C_{16}$ alkyl sulphate radicals. Such quaternary ammonium salts include tallow propane diammonium dichloride.

Preferred quaternary ammonium salts include dialkyldimethyl-ammonium chlorides, wherein the alkyl groups have from about 12 to about 22 carbon atoms and are derived from long-chain fatty acids, such as hydrogenated tallow fatty acid (tallow fatty acids yield quaternary compounds wherein $R^1$ and $R^2$ have predominately from 16 to 18 carbon atoms). A particularly preferred quaternary ammonium salt is 2-ethylhexyl alkyl ammonium methosulfate, commercially available from Akzo-Nobel as Arquad HTL8-MS®.

Cationic polymers may also be suitable and these can include Guar Hydroxypropyltrimonium chloride, Quaternium-19, -23, -40, -57, poly(dimethyldiallylammonium chloride), poly (dimethyl butenyl ammonium chloride)-, ω-bis(triethanolammonium chloride), poly (diallylpiperidinium chloride), poly (vinyl pyridinium chloride), quaternized poly (vinyl alcohol), quaternized poly (dimethylaminoethylmethacrylate) and mixtures thereof.

Levels of the electrolyte may range from about 0.001 to about 10%, preferably from about 0.05 to about 2%, optimally from about 0.1 to about 0.5% by weight.

Optional further components of compositions according to the present invention can include humectants such as water, glycerin, propylene glycol, sorbitol and dimethyl isosorbide. Amounts of these components may range from about 0.1 to about 30% by weight of the total composition.

Emollients such as fatty acid esters, mineral oil, silicone oil, lanolin and lanolin derivatives may also be present in amounts from about 0.01 to about 10% by weight of the total composition. Conditioning agents can be incorporated into the compositions, an example of which is a hydrolyzed protein.

The following examples will more fully illustrate selected embodiments of this invention. All parts, percentages and proportions referred to herein and in the appended claims are by weight of the total composition unless otherwise stated.

EXAMPLE 1

This Example illustrates three formulations spanning a range of different viscosities according to the present invention.

TABLE I

THICK LIQUID

| COMPONENT | WEIGHT % |
| --- | --- |
| Acetone | 75.0 |
| Propylene Carbonate | 10.5 |
| Water | 12.3 |
| Glycerin | 1.5 |
| Rheolate 5000 | 0.3 |
| Ethomeen C-25A | 0.3 |
| Arquad HTL8-MS | 0.1 |

TABLE II

GEL

| COMPONENT | WEIGHT % |
| --- | --- |
| Acetone | 75.0 |
| Propylene Carbonate | 10.5 |
| Water | 11.8 |
| Glycerin | 1.5 |
| Rheolate 5000 | 0.55 |
| Ethomeen C-25A | 0.55 |
| Arquad HTL8-MS | 0.1 |

TABLE III

CREAM

| COMPONENT | WEIGHT % |
| --- | --- |
| Acetone | 75.0 |
| Propylene Carbonate | 10.5 |
| Water | 9.9 |
| Lytron 621 | 1.0 |
| Glycerin | 1.5 |
| Rheolate 5000 | 1.0 |
| Ethomeen C-25A | 1.0 |
| Arquad HTL8-MS | 0.1 |

EXAMPLE 2

The thickened liquid, gel and cream formulations of Example 1 (but absent Arquad HTL8-MS®) were evaluated as polish removers in a clinical test by 40 women. The clinical results indicated a perceived negative with respect to efficacy (i.e. removal of lacquer). Although the invention is not to be held to any theory, it was thought that the addition of thickening agent reduced the polarity of acetone, thereby reducing its solvency.

Conductivity measurements were then conducted on Cutex® Regular (ingredients: 75% acetone, 10.5% propylene carbonate, 12.5% water, 0.75% glycerin, 0.75% diglycerin and 0.5% Ethomeen® C-25A) which was compared to the thick liquid (with 0.3% Rheolate® 5000) of Example 1 both with and without Arquad HTL8-MS at room temperature. The conductivity values were:

| FORMULATION | CONDUCTIVITY (μmhos) | LACQUER REMOVAL |
| --- | --- | --- |
| Cutex ® | 126 | excellent |
| Cutex (with Rheolate) | 25 | poor |
| Cutex (with Rheolate and Arquad) | 136 | good |

Lacquer removal was measured by an in vitro test to establish efficacy. Addition of the quat (Arquad) provided a significant improvement with respect to efficacy. Moreover, quaternary ammonium compounds often adversely interact with polymers to reduce viscosity. The combination of Rheolate® and Arquad® did not significantly decrease viscosity; original viscosity of 18.7 mPa-s was reduced only to a minor extent down to 16.6 mPa-s.

EXAMPLE 3

An ethyl acetate formulation according to the present invention is outlined below.

| COMPONENT | WEIGHT % |
| --- | --- |
| Ethyl Acetate | 80.0 |
| Ethanol | 12.5 |
| Castor Oil | 3.0 |
| Lanolin | 2.0 |
| Rheolate ® 5000 | 1.0 |
| Butyl Stearate | 0.5 |
| Quaternium-19 | 0.5 |
| Benzophenone-1 | 0.4 |
| Propylene Glycol | 0.1 |

EXAMPLE 4

This Example illustrates the use of Pemulen® as a thickening agent in compositions according to the present invention.

| COMPONENT | WEIGHT % |
| --- | --- |
| Acetone | 75.0 |
| Water | 23.9 |
| Pemulen ® (Cross-Linked Acrylic Acid/Acrylates) | 1.0 |
| Arquad ® HTL8-MS | 0.1 |

EXAMPLE 5

This Example illustrates use of Carbopol® 1382 as a thickening agent in conjunction with guar hydroxypropyltrimonium chloride as the electrolyte in a composition according to the present invention.

| COMPONENT | WEIGHT % |
| --- | --- |
| Acetone | 80.0 |
| Ethyl Acetate | 14.7 |
| Ethanol | 2.0 |
| Glycerin | 2.0 |
| Carbopol ® 1382 | 1.0 |

-continued

| COMPONENT | WEIGHT % |
| --- | --- |
| Guar Hydroxypropyltrimonium Chloride | 0.3 |

EXAMPLE 6

This Example illustrates a formulation with magnesium bromide, an inorganic electrolyte, according to the present invention.

| COMPONENT | WEIGHT % |
| --- | --- |
| Acetone | 75.0 |
| Water | 23.0 |
| Ethomeen ® C-25A | 1.1 |
| Rheolate ® 5000 | 0.6 |
| Magnesium Bromide | 0.3 |

EXAMPLE 7

This Example illustrates hydroxypropyl methyl cellulose as a thickening agent in combination with aluminum sulphate as the electrolyte in a composition according to the present invention.

| COMPONENT | WEIGHT % |
| --- | --- |
| Acetone | 75.0 |
| Water | 22.9 |
| Glycerin | 0.8 |
| Diglycerin | 0.8 |
| Hydroxypropyl Methyl Cellulose | 0.3 |
| Aluminum Sulfate | 0.2 |
| Gelatin | 0.001 |

EXAMPLE 8

This Example illustrates the use of methyl vinyl ether/maleic anhydride copolymer crosslinked as the thickening agent in combination with Quaternium-23 as the electrolyte in a composition according to the present invention.

| COMPONENT | WEIGHT % |
| --- | --- |
| Methyl Ethyl Ketone | 80.0 |
| Water | 16.8 |
| Glycerin | 1.0 |
| Diglycerin | 1.0 |
| Methyl Vinyl Ether/Maleic Anhydride Copolymer | 1.0 |

-continued

| COMPONENT | WEIGHT % |
|---|---|
| Crosslinked Quaternium-23 | 0.2 |

EXAMPLE 9

This Example illustrates xanthan gum as a thickening agent in combination with lithium chloride as the electrolyte in a composition according to the present invention.

| COMPONENT | WEIGHT % |
|---|---|
| Acetone | 85.0 |
| Water | 11.2 |
| Lanolin | 3.0 |
| Xanthan Gum | 1.5 |
| Lithium Chloride | 0.3 |

The foregoing description and Examples illustrate select embodiments of the present invention and in light thereof various modifications will be suggested to one skilled in the art, all of which are within the spirit and purview of this invention.

What is claimed is:

1. A polish-lacquer removing composition comprising:
   (i) from about 50 to about 85% by weight of a volatile solvent having 2 to 10 carbon atoms and exhibiting a vapor pressure of more than 0.1 mm at 20° C.;
   (ii) a thickening agent present in an effective amount to provide the composition with a viscosity ranging between 250 and 10,000 mPa-sec measured at 10 sec$^{-1}$ on a Haake CV 20 Rheometer; and
   (iii) 2-ethylhexyl alkyl ammonium methosulfate present in an effective amount to raise conductivity of the composition to above 80 μmhos.

2. A composition according to claim 1 wherein the volatile organic solvent is selected from the group consisting of acetone, ethyl acetate and combinations thereof.

3. A composition according to claim 1 wherein the thickening agent is an acrylate/vinyl acetate cross polymer.

\* \* \* \* \*